United States Patent
Ikhlef

(10) Patent No.: US 8,204,171 B2
(45) Date of Patent: Jun. 19, 2012

(54) MULTI-FACETED TILEABLE DETECTOR FOR VOLUMETRIC COMPUTED TOMOGRAPHY IMAGING

(75) Inventor: Abdelaziz Ikhlef, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 128 days.

(21) Appl. No.: 12/901,658

(22) Filed: Oct. 11, 2010

(65) Prior Publication Data

US 2012/0087465 A1 Apr. 12, 2012

(51) Int. Cl.
*A61B 6/00* (2006.01)
(52) U.S. Cl. .............................. 378/4; 378/19
(58) Field of Classification Search ................ 378/4, 19
See application file for complete search history.

(56) References Cited

U.S. PATENT DOCUMENTS

| | | | |
|---|---|---|---|
| 4,982,096 A * | 1/1991 | Fujii et al. ..................... | 250/367 |
| 5,757,878 A * | 5/1998 | Dobbs et al. .................... | 378/19 |
| 5,781,606 A * | 7/1998 | Dobbs et al. .................... | 378/19 |
| 6,584,167 B1 | 6/2003 | Ikhlef et al. | |
| 6,979,826 B2 | 12/2005 | Ikhlef | |
| 7,149,284 B2 | 12/2006 | Ikhlef | |
| 7,166,844 B1 * | 1/2007 | Gormley et al. ........... | 250/358.1 |
| 7,233,640 B2 | 6/2007 | Ikhlef et al. | |
| 7,308,074 B2 * | 12/2007 | Jiang et al. ...................... | 378/19 |
| 7,399,119 B2 | 7/2008 | Chao et al. | |
| 7,455,454 B2 | 11/2008 | Ikhlef et al. | |
| 7,602,951 B2 | 10/2009 | Hsieh et al. | |
| 7,620,143 B2 | 11/2009 | Ikhlef et al. | |
| 2007/0121781 A1 | 5/2007 | Meirav et al. | |

FOREIGN PATENT DOCUMENTS

| | | |
|---|---|---|
| EP | 1769744 A2 | 4/2007 |
| WO | 2010007544 A1 | 1/2010 |

OTHER PUBLICATIONS

European Search Report and Search Opinion from corresponding EP Application No. 11183686.2 dated Feb. 1, 2012.

\* cited by examiner

*Primary Examiner* — Alexander H Taningco
(74) *Attorney, Agent, or Firm* — Ziolkowski Patent Solutions Group, SC

(57) ABSTRACT

A system and method for CT image acquisition with increased slice acquisition and minimal image data degradation is provided. The system includes an x-ray projection source positioned that projects a cone beam of x-rays from a focal spot of the x-ray projection source toward an object and a plurality of detector modules positioned on the rotatable gantry to receive x-rays attenuated by the object. Each of the detector modules includes a module frame having a top surface that includes a plurality of facets formed thereon constructed so as to be oriented at differing angles relative to the focal spot and a plurality of sub-modules positioned on the plurality of facets to receive the x-rays attenuated by the object and to convert the x-rays to electrical signals, with each sub-module being oriented at an angle relative to the focal spot based on a respective facet on which the sub-module is mounted.

20 Claims, 5 Drawing Sheets

MULTI-FACETED TILEABLE DETECTOR FOR VOLUMETRIC COMPUTED TOMOGRAPHY IMAGING

BACKGROUND OF THE INVENTION

Embodiments of the invention relate generally to radiographic detectors for diagnostic imaging and, more particularly, to a Computed Tomography (CT) detector module having a multi-faceted construction that provides for increased slice acquisition with minimal image data degradation.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector and rejecting scatter from the patient, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

In the last decade, the development of volumetric or cone-beam CT (VCT) technology has led to a rapid increase in the number of slices (Z-axis) used in CT detectors. Indeed, the detectors used in VCT are enabling more and more coverage in patient scanning by increasing the patient area exposed. In order to accommodate such coverage, the width of CT detectors has been increased in the Z-axis (i.e., direction of patient length). The x-ray detectors of current state of the art CT systems are composed of a 2D array of scintillating pixels, coupled to a 2D array of silicon photodiodes, with the typical array being sized so as to be capable of providing for acquisition of 64 slices (i.e., array size of 40 mm at ISO in case of GE scanner).

Recently, however, the need for cardiac imaging has become more and more of interest and imaging of the heart within one rotation has become a requirement. In order to image the heart in one rotation, the detector array size needs to be ~160 mm at ISO to cover the full organ in half scan, which is equivalent to a detector of 256 slices in our case. However, increasing the coverage of the detector in the Z-axis beyond 64 slices up to 256 slices might lead to a degradation in performance of the detector. That is, the performance of the detector pixels, especially those pixels at a greater distance from a centerline of the detector along the Z-axis, will be degraded because of the angle at which such pixels receive x-rays from the cone beam. At a certain position along the Z-axis, the primary beam of x-rays will cross two contiguous pixels in the Z-direction, thereby inducing a significant crosstalk from slice to slice, spectral non-linearity because of the beam hardening with the pixels, slice profile degradation, and Modulation transfer function (MTF) deterioration, collectively known as "parallax." This parallax caused by the increased number of slices can lead to artifacts being present in the reconstructed CT image, thereby presenting a significant drawback to image quality provided by a 256 slice detector and beyond.

Therefore, it would be desirable to design a CT detector that provides for VCT cardiac imaging by accommodating data acquisition of up to 256 slices. It would also be desirable for such a CT detector to minimize the parallax effect in such a detector, so as to provide for high quality image reconstruction of the cardiac region of a patient.

BRIEF DESCRIPTION OF THE INVENTION

The invention is a directed apparatus for CT image acquisition that provides for increased slice acquisition with minimal image data degradation. A detector module having a multi-faceted construction is provided, with a plurality of facets on the module being constructed so as to be oriented at differing angles relative to an x-ray source focal spot. Detector sub-modules are positioned on the angled facets to receive x-rays attenuated by an object and to convert the x-rays to electrical signals, with the angling of the detector sub-modules relative to the focal spot serving to minimize image data degradation.

In accordance with one aspect of the invention, a CT system includes a rotatable gantry having an opening to receive an object to be scanned, an x-ray projection source positioned on the rotatable gantry that projects a cone beam of x-rays from a focal spot of the x-ray projection source toward the object, and a plurality of detector modules positioned on the rotatable gantry and configured to receive x-rays attenuated by the object. Each of the plurality of detector modules further includes a module frame having a top surface that includes a plurality of facets formed thereon that are constructed so as to be oriented at differing angles relative to the focal spot and a plurality of sub-modules positioned on the plurality of facets to receive the x-rays attenuated by the object and to convert the x-rays to electrical signals, with each sub-module being oriented at an angle relative to the focal spot based on a respective facet on which the sub-module is mounted. The CT system also includes a data acquisition system (DAS) connected to the plurality of sub-modules to receive the electrical signals therefrom.

In accordance with another aspect of the invention, a detector module for receiving x-rays attenuated by an object during a CT scan procedure includes a module frame having a non-planar top surface that includes a plurality of facets formed thereon in a stepped configuration, with the plurality of facets being aligned along a Z-axis of the detector. The detector module also includes a plurality of sub-modules positioned on the plurality of facets to receive the x-rays attenuated by the object and to convert the x-rays to electrical signals and a data acquisition system (DAS) connected to the plurality of sub-modules to receive the electrical signals therefrom.

In accordance with yet another aspect of the invention, a CT system includes a rotatable gantry having an opening to receive an object to be scanned, an x-ray projection source positioned on the rotatable gantry that projects a cone beam of x-rays from a focal spot of the x-ray projection source toward the object, and a plurality of detector modules positioned on the rotatable gantry to receive x-rays attenuated by the object. Each of the plurality of detector modules comprises a multi-faceted detector module including a plurality of sub-modules aligned along a Z-axis, with each of the plurality of sub-modules being oriented at an optimized angle relative to the focal spot of the x-ray projection source based on its position on the multi-faceted detector module along the Z-axis.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of the invention is described with respect to a 256 slice computed tomography (CT) system. However, as will be explained in detail below, the invention is equally applicable for use with other multi-slice configurations between sixty-four slices and 256 slices, and beyond. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
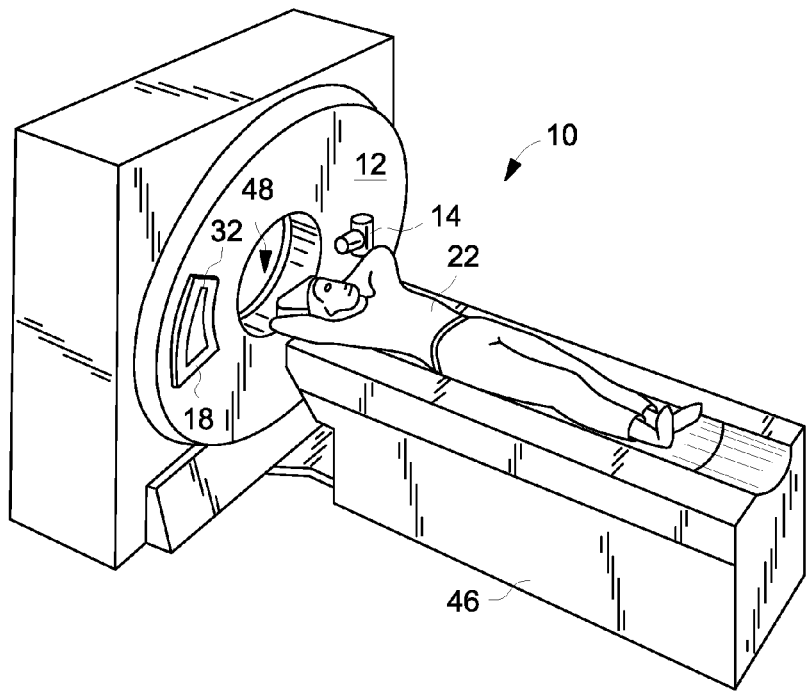
FIG. 1 is a pictorial view of a CT imaging system.
Figure 2:
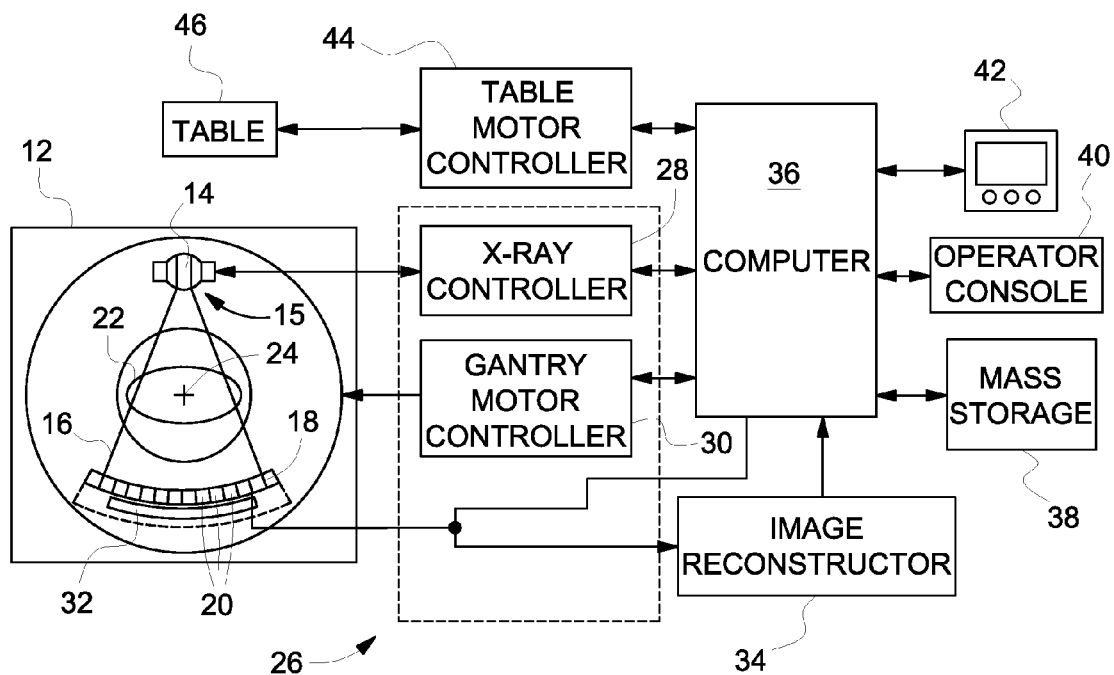
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays from a focal spot 15 of the source 14 and toward a detector assembly 18 on the opposite side of the gantry 12. Referring now to FIG. 2, detector assembly 18 is formed by a plurality of detector modules 20 and data acquisition systems (DAS) 32. The plurality of detector modules 20 sense the projected x-rays 16 that pass through a medical patient 22, and DAS 32 converts the data to digital signals for subsequent processing. Each detector module 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
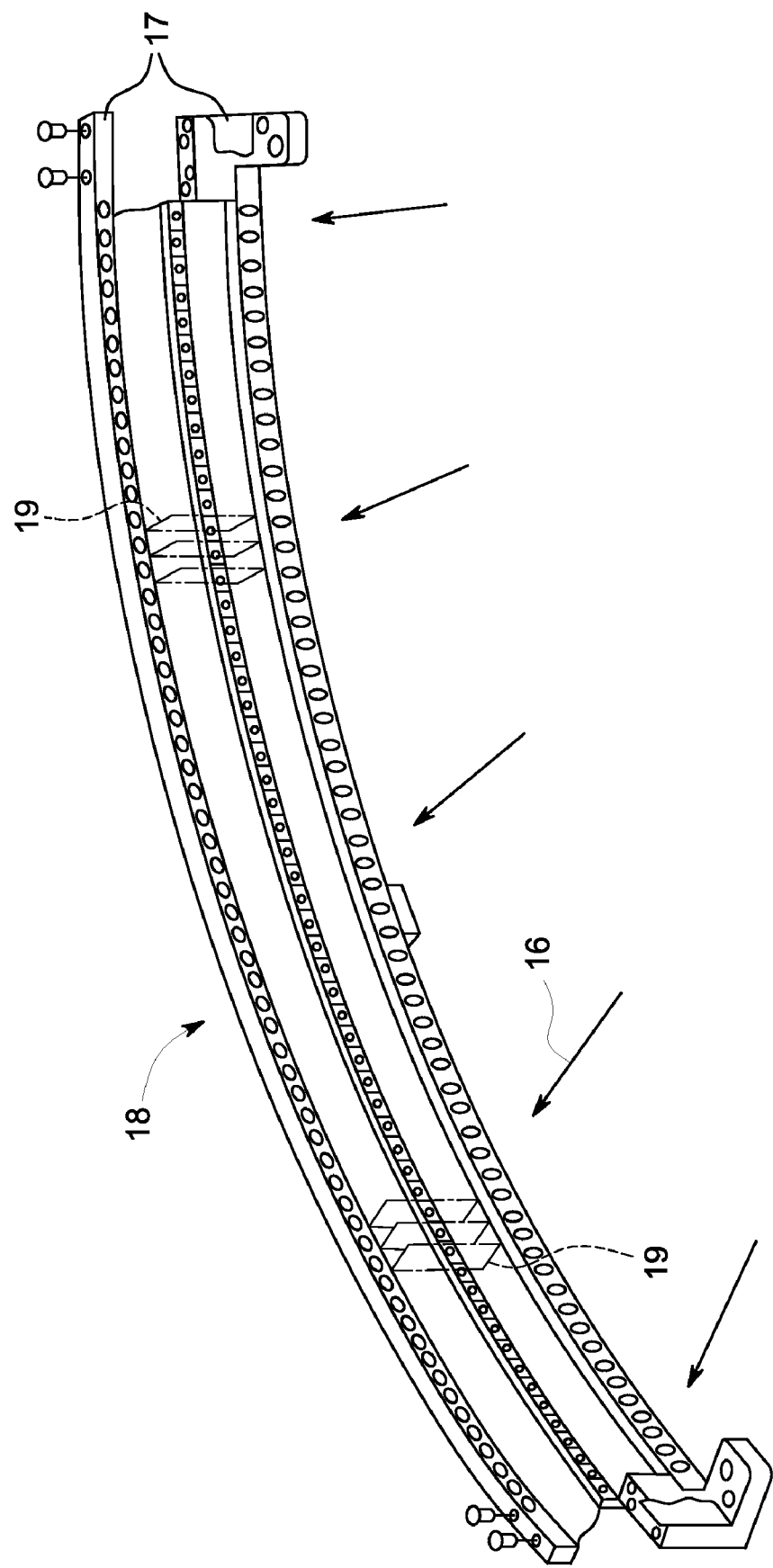
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector module 20 of FIG. 4 positioned on detector assembly 18. According to an embodiment of the invention, detector assembly 18 includes 57 detector modules 20, each detector module 20 having an array size of 256×16 of pixel elements, as will be explained in detail below. As a result, detector assembly 18 has 256 rows and 912 columns (16×57 detectors), which allows 256 simultaneous slices of data to be collected with each rotation of gantry 12.

Figure 4:
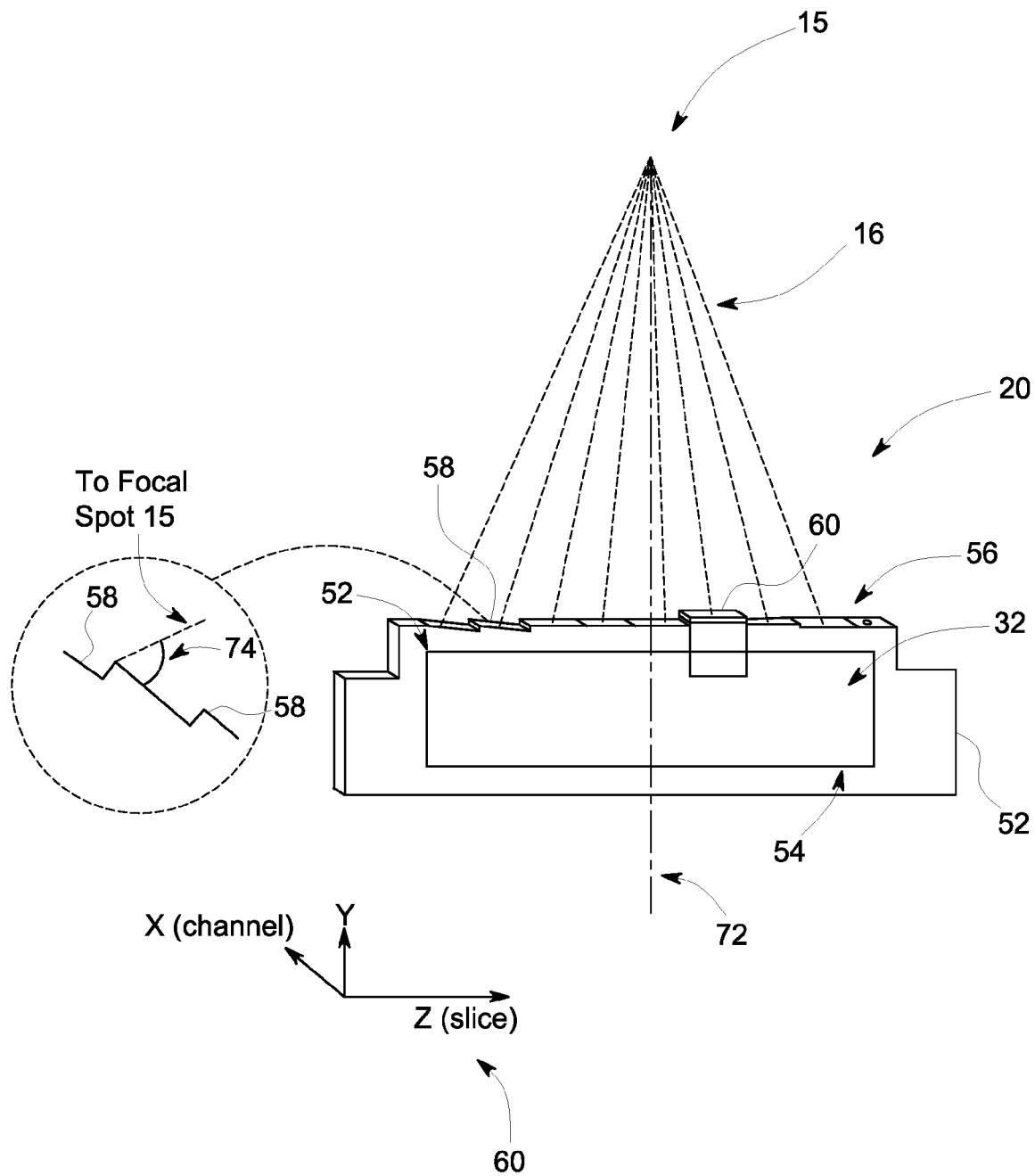
FIG. 4 is a perspective view of a detector module according to an embodiment of the invention.

Referring to FIG. 4, construction of a detector module 20 is shown according to an exemplary embodiment of the invention. The detector module 20 includes a module frame 52 having an opening therein to accommodate DAS 32. A top surface 56 of module frame 52 is constructed to have a stepped configuration and thus includes a plurality of facets 58 thereon. The facets 58 are aligned lengthwise along the module frame 52, along the Z-axis 60. According to one embodiment of the invention, eight facets 58 are formed on the top surface 56 of module frame 52.

As shown in FIG. 4, each facet 58 formed on top surface 56 of module frame 52 is sized and configured to accommodate a detector sub-module 60 to receive and process x-rays that attenuate through a patient or object. While only a single sub-module 60 is shown as being included on detector module 20, it is recognized that a sub-module 60 could be placed on each/all facets 58 of module frame 52 such that a plurality of sub-modules 60 are included in detector module 20 (e.g., eight sub-modules 60).

Figure 5:
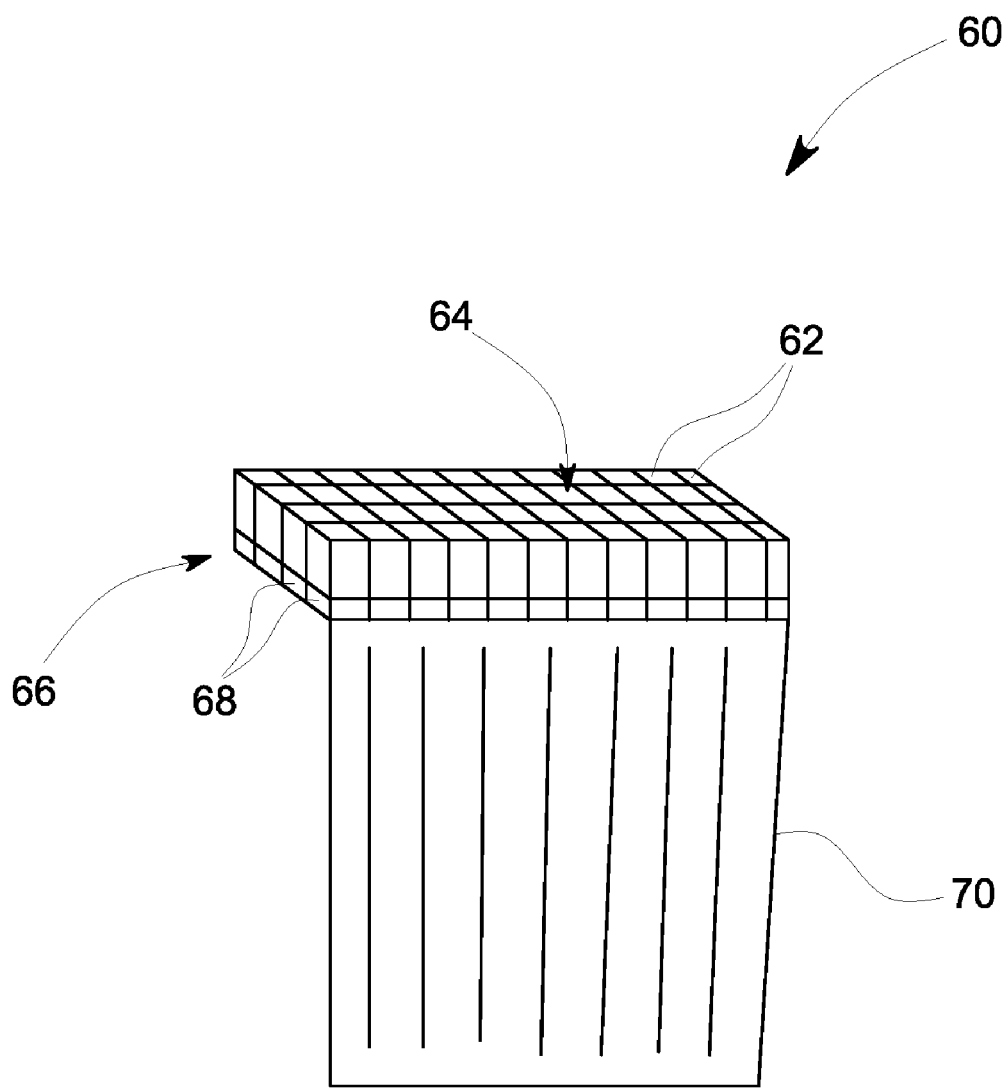
FIG. 5 is a perspective view of a detector sub-module for use with the detector module of FIG. 4 according to an embodiment of the invention.

A detailed view of a sub-module 60 is shown in FIG. 5 according to an embodiment of the invention. Sub-module 60 includes a number of scintillator detector elements or pixels 62 arranged in a scintillating pack array 64. According to one embodiment, the scintillating pack array 64 is composed of a 32×16 array of detector elements 62, such that each scintillating pack array 64 includes 32 slices. The scintillating pack array 64 is positioned on a backlit diode array 66 formed of a plurality of diode elements or pixels 68 (i.e., a 32×16 array of diodes). Detector elements 62 are optically coupled to backlit diode array 66, and backlit diode array 66 is in turn electrically coupled to flex circuits 70 that are attached to a face of the diode array 66 and to DAS 32 (FIG. 4). In the operation of one embodiment, x-rays impinging within detector elements 62 to generate photons that traverse pack array 64, thereby generating an analog signal which is detected on a diode 68 within backlit diode array 66. The analog signal generated is carried from backlit diode array 66, through flex circuits 70, to DAS 32 wherein the analog signal is converted to a digital signal.

According to embodiments of the invention, the size of sub-module 60 can be varied in order to optimize for performance and scalability. The sub-module may, for example, have a size of 20 mm in length (i.e., 20 mm along the Z-axis). It is recognized, however, that the sub-module 60 can be from 10 mm in length up to 40 mm in length depending on the exact configuration of detector module 20, such as the size of each facet 58. Furthermore, while sub-module 60 is shown as including scintillator array 64 and photodiode array 66, it is recognized that such elements/materials in sub-module 60 could be replaced with a direct conversion material that directly converts x-rays into electrical signals, such as cadmium-telluride (CdTe) or cadmium-zinc-telluride (CZT).

Referring again to FIG. 4, it is seen that eight facets 58 are aligned lengthwise along the module frame 52, along the Z-axis, thus allowing for an increase in the number of slices that can be obtained during CT imaging. According to one embodiment of the invention, detector module 20 can include eight sub-modules 60, with each sub-module 60 positioned on a respective facet 58, such that the summation of each 32×16 array of detector elements 62 in each sub-module 60 results in an array size of 256×16 of detector elements 62 for detector module 20. As a result, detector module 20 provides for 256 simultaneous slices of data to be collected with each rotation of gantry 12 (FIG. 1). Beneficially, however, the sub-modules 60 of detector module 20 are tileable, in that the number of sub-modules 60 included in detector module 20 can be varied as desired. That is, according to an embodiment of the invention, only four sub-modules 60 may be included in detector module 20, for example. In an embodiment where only four sub-modules 60 are included in detector module 20, the sub-modules 60 would be positioned on facets 58 in a symmetrical fashion about a centerline 72 of the detector module along the Z-axis. For sub-modules 60 sized to have a length of 20 mm, it is thus recognized that a detector module 20 can be built having a length from 20 to 160 mm based on populating and depopulating sub-modules 60 on the Z-axis.

In including a larger number of sub-modules 60 in detector module 20, such as eight sub-modules 60 to form a 256 slice detector, it is recognized that as the length of the detector module 20 increases in the Z-direction (i.e., length of the array of detector elements/pixels 62, based on the number of sub-modules 60), that the quality of CT data acquired by the detector module 20 may decrease. That is, the performance of the detector elements/pixels 62 in the Z-axis will be degraded because of the cone angle at which x-rays 16 are received. At certain positions along the Z-axis, the primary x-ray beam 16 will cross two contiguous pixels 62 in the Z-direction, resulting in significant x-ray crosstalk of the primary beam 16 from one slice to its neighbor along the Z-axis, spectral non-linearity because of beam hardening with the pixels, slice profile degradation, and modulation transfer function (MTF) deterioration, with these quality issues collectively referred to as "parallax." This parallax experienced in detector module 20 may lead to significant artifacts in a reconstructed CT image.

Accordingly, detector module 20 is configured such that each sub-module 60 is positioned at a certain angle with respect to the x-ray beam focal spot 15 in order to avoid the parallax effect. In order to position sub-modules 60 at a desired angle relative to the focal spot 15, each facet 58 of the top surface 56 of module frame 52 is oriented at a given angle 74 to the focal spot 15. The angle 74 at which each facet 58 is formed is individually optimized such that the slices of sub-modules 60 are minimally affected by the parallax phenomenon (i.e., minimizes x-ray crosstalk between slices, spectral non-linearity, slice profile degradation, and MTF deterioration), with the angle of each facet 58 with respect to the focal spot 15 being varied/determined as a function of the performance desired and the specific image quality parameter to improve. According to embodiments of the invention, the angle 74 at which each facet 58 is oriented relative to the focal spot 15 can vary so as to fall within the range of angles falling between facet 58 being laid flat on top surface 56 and facet 58 being angled so as to be perpendicular to focal spot 15 (i.e., perpendicular to an x-ray beam 16 emitted from focal spot 15 and received by the sub-module 60 positioned on a respective facet 58). In general, the angle 74 of a particular facet 58 relative to the focal spot 15 will increase the further the facet 58 is from the centerline 72 of detector module 20. Thus, the outermost facets 58 on module frame 52 may be oriented at a greater angle relative to focal spot 15 than the middle facets 58 on module frame 52 adjacent to the centerline 72, which may be oriented almost flat on top surface 56. Sub-modules 60 are then positioned on facets 58 and secured thereto so as to be positioned at desired angles formed by their corresponding facet 58, such as via an adhesive, screws, or any other acceptable fastening method.

The angling of sub-modules 60 relative to focal spot 15, by way of angled facets 58 on module frame 52, thus provides for a detector module 20 that is non-sensitive to focal spot motion in the Z-axis. The parallax phenomenon is minimized in detector module 20, thereby providing for the crosstalk, spectral linearity, and slice profiles of the outermost sub-modules 60 to be consistent with the innermost sub-modules 60 and similar to VCT specifications typically associated existing 64 slice detector module architecture. As set forth above, the angle of each facet with respect to the focal spot is varied/determined as a function of the performance desired and the specific image quality parameter to improve.

Figure 6:
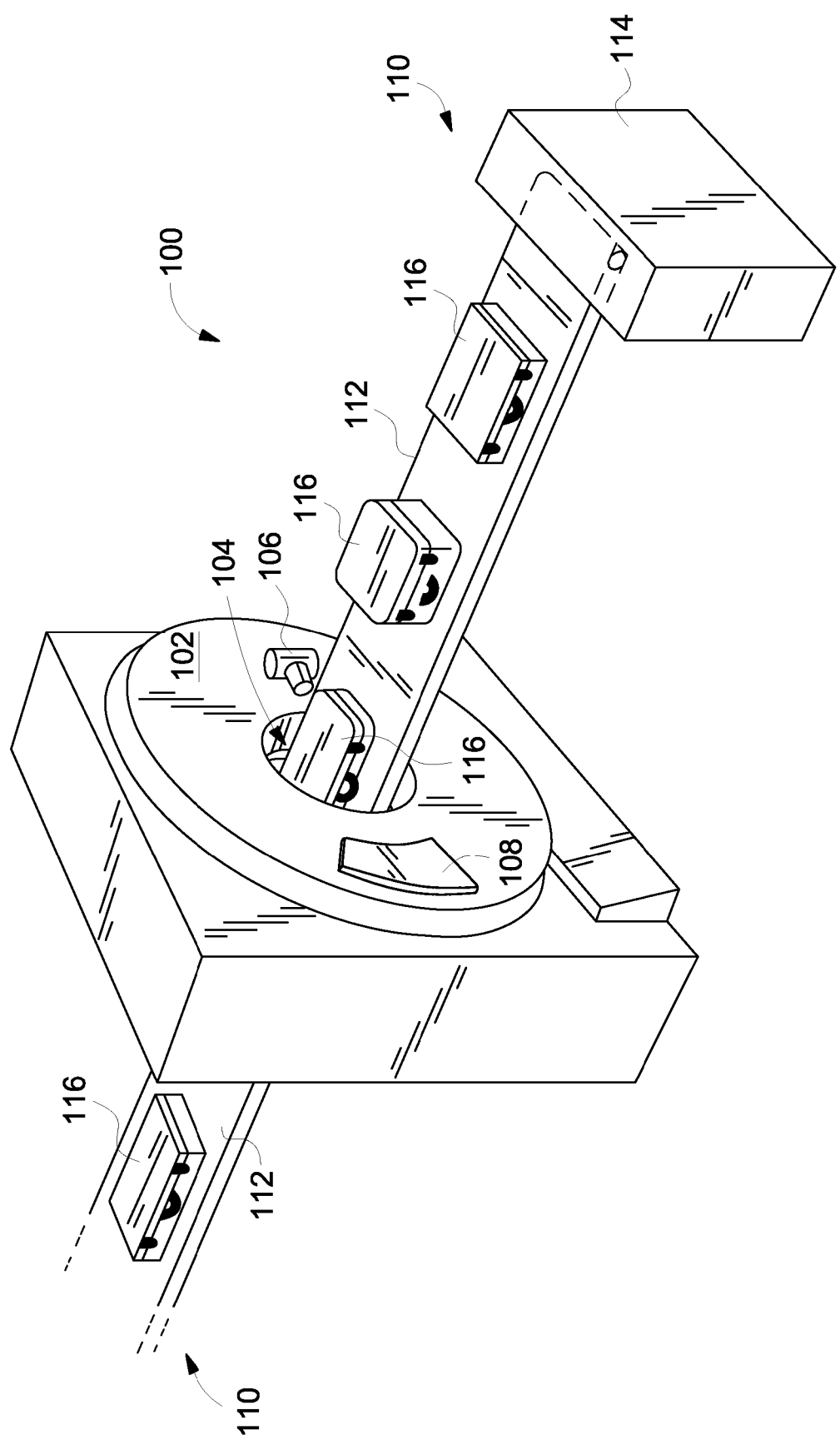
FIG. 6 is a pictorial view of a CT system for use with a non-invasive package inspection system.

Referring now to FIG. 6, package/baggage inspection system 100 includes a rotatable gantry 102 having an opening 104 therein through which packages or pieces of baggage may pass. The rotatable gantry 102 houses a high frequency electromagnetic energy source 106 as well as a detector assembly 108 having detector modules 20 similar to that shown in FIGS. 4 and 5. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

According to an embodiment of the invention, incorporation of detector modules 20 (FIG. 4) into the package/baggage inspection system 100 provides for decreased scanning time of packages 116. That is, detector modules 20 (FIG. 4) allow for system 100 to scan a greater volume of the packages in a single revolution of gantry 102, as 256 slices can be acquired by detector modules 20. A more efficient scanning of packages 116 by package/baggage inspection system 100 is thus accomplished by way of detector modules 20 (FIG. 4) being incorporated into the system 100.

Therefore, according to one embodiment of the invention, a CT system includes a rotatable gantry having an opening to receive an object to be scanned, an x-ray projection source positioned on the rotatable gantry that projects a cone beam of x-rays from a focal spot of the x-ray projection source toward the object, and a plurality of detector modules positioned on the rotatable gantry and configured to receive x-rays attenuated by the object. Each of the plurality of detector modules further includes a module frame having a top surface that includes a plurality of facets formed thereon that are constructed so as to be oriented at differing angles relative to the focal spot and a plurality of sub-modules positioned on the plurality of facets to receive the x-rays attenuated by the object and to convert the x-rays to electrical signals, with each sub-module being oriented at an angle relative to the focal spot based on a respective facet on which the sub-module is mounted. The CT system also includes a data acquisition system (DAS) connected to the plurality of sub-modules to receive the electrical signals therefrom.

According to another embodiment of the invention, a detector module for receiving x-rays attenuated by an object during a CT scan procedure includes a module frame having a non-planar top surface that includes a plurality of facets formed thereon in a stepped configuration, with the plurality of facets being aligned along a Z-axis of the detector. The detector module also includes a plurality of sub-modules positioned on the plurality of facets to receive the x-rays attenuated by the object and to convert the x-rays to electrical signals and a data acquisition system (DAS) connected to the plurality of sub-modules to receive the electrical signals therefrom.

According to yet another embodiment of the invention, a CT system includes a rotatable gantry having an opening to receive an object to be scanned, an x-ray projection source positioned on the rotatable gantry that projects a cone beam of x-rays from a focal spot of the x-ray projection source toward the object, and a plurality of detector modules positioned on the rotatable gantry to receive x-rays attenuated by the object. Each of the plurality of detector modules comprises a multi-faceted detector module including a plurality of sub-modules aligned along a Z-axis, with each of the plurality of sub-modules being oriented at an optimized angle relative to the focal spot of the x-ray projection source based on its position on the multi-faceted detector module along the Z-axis.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A CT system comprising:
    a rotatable gantry having an opening to receive an object to be scanned;
    an x-ray projection source positioned on the rotatable gantry that projects a cone beam of x-rays from a focal spot of the x-ray projection source toward the object; and
    a plurality of detector modules positioned on the rotatable gantry and configured to receive x-rays attenuated by the object, wherein each of the plurality of detector modules comprises:
        a module frame having a top surface that includes a plurality of facets formed thereon, wherein the plurality of facets are constructed so as to be oriented at differing angles relative to the focal spot;
        a plurality of sub-modules positioned on the plurality of facets to receive the x-rays attenuated by the object and to convert the x-rays to electrical signals, wherein each sub-module is oriented at an angle relative to the focal spot based on a respective facet on which the sub-module is mounted; and
        a data acquisition system (DAS) connected to the plurality of sub-modules to receive the electrical signals therefrom.

2. The CT system of claim 1 wherein the plurality of facets are aligned along a Z-axis, the Z-axis being a direction of travel of the object through the CT system.

3. The CT system of claim 1 wherein the top surface of the module frame is constructed to have a stepped configuration such that outermost sub-modules in the plurality of sub-modules are positioned at a different height relative to centermost sub-modules in the plurality of sub-modules.

4. The CT system of claim 1 wherein the angle of each of the plurality of facets relative to the focal spot ranges between being laid flat on the top surface of the module frame and being angled so as to be perpendicular to the focal spot.

5. The CT system of claim 1 wherein the plurality of facets comprises eight facets.

6. The CT system of claim 1 wherein the plurality of sub-modules comprise tileable sub-modules that are selectively addable to the facets of the module frame, such that the plurality of sub-modules comprises a number of sub-modules less than or equal to a number of facets in the plurality of facets.

7. The CT system of claim 1 wherein each of the plurality of sub-modules comprises:
    a scintillator array having a plurality of scintillator pixels configured to receive x-rays attenuated through the object;
    a photodiode array optically coupled to the scintillator array and comprising a plurality of photodiodes configured to detect light output from a corresponding scintillator pixel; and
    a flex circuit connected to the photodiode array to receive electrical signals therefrom and transfer the electrical signals to the DAS.

8. The CT system of claim 7 wherein the flex circuit is configured to clamp the sub-module to the module frame.

9. The CT system of claim 7 wherein each of the plurality of sub-modules comprises a 32 by 16 array of scintillator pixels, such that each of the plurality of sub-modules is configured to acquire 32 image data slices.

10. The CT system of claim 1 wherein the detector module is configured to acquire 256 image data slices during a single rotation of the x-ray source about the rotatable gantry.

11. A detector module for receiving x-rays attenuated by an object during a CT scan procedure, the detector module comprising:
    a module frame having a non-planar top surface that includes a plurality of facets formed thereon in a stepped configuration, the plurality of facets being aligned along a Z-axis of the detector;
    a plurality of sub-modules positioned on the plurality of facets to receive the x-rays attenuated by the object and to convert the x-rays to electrical signals; and
    a data acquisition system (DAS) connected to the plurality of sub-modules to receive the electrical signals therefrom.

12. The detector module of claim 11 wherein the plurality of facets are constructed so as to be oriented at differing angles relative to a focal spot of an x-ray projection source that projects x-rays toward the object.

13. The detector module of claim 12 wherein the plurality of facets includes at least a pair of inner facets positioned adjacent a centerline of the detector module on either side of the centerline and a pair of outer facets positioned distal from the centerline on either side of the pair of inner facets, and wherein each of the pair of outer facets has an angle relative to the focal spot that is greater than an angle of each of the pair of inner facets.

14. The detector module of claim 12 wherein each of the plurality of sub-modules comprises an array of detector pixels, and wherein the angle of each of the plurality of facets on the module frame is configured to focalize a respective sub-module at a specified angle with respect to the focal spot so as to minimize crosstalk in the array of detector pixels in the Z-axis.

15. The detector module of claim 11 wherein each of the plurality of sub-modules is selectively addable to and removable from the module frame, such that a number of sub-modules included in the detector module is controllable.

16. A CT system comprising:
   a rotatable gantry having an opening to receive an object to be scanned;
   an x-ray projection source positioned on the rotatable gantry that projects a cone beam of x-rays from a focal spot of the x-ray projection source toward the object; and
   a plurality of detector modules positioned on the rotatable gantry and configured to receive x-rays attenuated by the object, wherein each of the plurality of detector modules comprises a multi-faceted detector module including a plurality of sub-modules aligned along a Z-axis;
   wherein each of the plurality of sub-modules is oriented at an optimized angle relative to the focal spot of the x-ray projection source based on its position on the multi-faceted detector module along the Z-axis.

17. The CT system of claim 16 wherein the multi-faceted detector module comprises a module frame having a top surface that includes a plurality of facets formed thereon, each of the plurality of facets being sized to receive a single sub-module thereon.

18. The CT system of claim 16 wherein the top surface of the module frame is constructed to have a stepped configuration such that outermost sub-modules in the plurality of sub-modules are positioned at a different height relative to centermost sub-modules in the plurality of sub-modules.

19. The CT system of claim 16 wherein each of the plurality of sub-modules comprises an array of detector pixels configured to receive x-rays attenuated through the object and convert the x-rays to electrical signals, the array of detector pixels comprising a 32×16 array such that each of the plurality of sub-modules acquires 32 image data slices during a single rotation of the x-ray source about the rotatable gantry.

20. The CT system of claim 19 wherein the detector module comprises eight sub-modules, such that the detector module acquires 256 image data slices during a single rotation of the x-ray source about the rotatable gantry.

* * * * *